(12) United States Patent
Lange

(10) Patent No.: US 7,728,164 B2
(45) Date of Patent: Jun. 1, 2010

(54) PROCESS FOR THE PREPARATION OF PROPYLENE CARBONATE

(75) Inventor: Jean-Paul Lange, Amsterdam (NL)

(73) Assignee: Shell Oil Company, Houston, TX (US)

( * ) Notice: Subject to any disclaimer, the term of this patent is extended or adjusted under 35 U.S.C. 154(b) by 1360 days.

(21) Appl. No.: 10/880,079

(22) Filed: Jun. 29, 2004

(65) Prior Publication Data

US 2005/0014956 A1    Jan. 20, 2005

(30) Foreign Application Priority Data

Jun. 30, 2003 (EP) .................................. 03254161

(51) Int. Cl.
*C07C 69/96* (2006.01)
(52) U.S. Cl. .................................................. 558/260
(58) Field of Classification Search .................. 558/260
See application file for complete search history.

(56) References Cited

U.S. PATENT DOCUMENTS

| 2,994,705 | A |   | 8/1961 | Crosby et al. ............. 260/340.2 |
| 4,160,116 | A | * | 7/1979 | Mieno et al. ................. 568/867 |
| 4,400,559 | A |   | 8/1983 | Bhise ........................ 568/858 |
| 4,434,105 | A | * | 2/1984 | Buysch et al. ............... 558/260 |
| 5,153,333 | A |   | 10/1992 | Schubert et al. |
| 6,080,897 | A |   | 6/2000 | Kawabe |
| 6,384,240 | B1 | * | 5/2002 | Machac et al. .............. 549/230 |
| 6,399,536 | B2 | * | 6/2002 | Kim et al. ................... 502/169 |
| 6,897,343 | B2 | * | 5/2005 | Von Hebel et al. .......... 568/867 |
| 2003/0045739 | A1 |   | 3/2003 | Buchanan et al. ........... 558/277 |

FOREIGN PATENT DOCUMENTS

| EP | 478073 | 4/1992 |
| EP | 776890 | 6/1997 |
| GB | 2035294 | 6/1980 |
| JP | 6-238165 | 8/1994 |
| WO | 99/57108 | 11/1999 |

OTHER PUBLICATIONS

International Search Report dated Oct. 20, 2004 (PCT/EP2004/051270).
International Preliminary Examination Report dated Oct. 14, 2005 (PCT/EP2004/051270).

* cited by examiner

*Primary Examiner*—James O Wilson
*Assistant Examiner*—Ebenezer Sackey

(57) ABSTRACT

The invention relates to a process for the preparation of propylene carbonate, which process involves contacting propylene oxide with carbon dioxide at a temperature of from 150° C. to 250° C. in the presence of a recycled tetraalkylphosphonium bromide catalyst.

14 Claims, No Drawings

PROCESS FOR THE PREPARATION OF PROPYLENE CARBONATE

FIELD OF THE INVENTION

The present invention relates to a process for the preparation of a propylene carbonate by reacting propylene oxide with carbon dioxide.

BACKGROUND OF THE INVENTION

Propylene carbonates are important intermediates in a number of different processes, for instance, as the replacement of highly toxic phosgene as carbonylating agents in processes such as the production of isocyanates or polycarbonates.

Another important use of propylene carbonates is the production of 1,2-propanediol by catalyzed hydrolysis. The propylene carbonates can also be used for the preparation of dimethyl carbonate, which has raised interest for use as octane enhancers in fuels as a replacement for methyl tert-butyl ether.

It has been found advantageous if the process can be carried out at a relatively high temperature such as of from 150 to 250° C. while the catalyst is recycled. It was found that such process makes efficient use of the starting compounds while an efficient heat-integration is possible. However, the combination of high temperature and catalyst recycle requires the catalyst to be very stable.

U.S. Pat. No. 5,153,333 describes a process for the conversion of epoxy resins at a temperature of from 60 to 160° C. with the help of quaternary phosphonium compounds. The catalyst remains in the final product in the exemplified process.

Phosphoniumbromide catalysts are mentioned in prior art such as U.S. Pat. No. 2,994,705, U.S. Pat. No. 4,434,105, WO-A-99/57108 and EP-A-776,890. However, there is no teaching in any of these documents on what catalyst is to be used if the propylene carbonate manufacture is to be carried out a temperature of from 150 to 250° C. and with recycle of the catalyst.

SUMMARY OF THE INVENTION

Accordingly, the present invention is directed to a process for the preparation of propylene carbonate, which process comprises contacting propylene oxide with carbon dioxide at a temperature of from 150° C. to 250° C. in the presence of a recycled tetraalkylphosphonium bromide catalyst of the formula $R^1R^2R^3R^4PBr$ (I).

Surprisingly, it was found that this specific phosphonium catalyst can be recycled after having been used at high temperature. A catalyst can only be subjected to such demanding conditions if it is very stable.

In the subject process, propylene oxide is reacted with carbon dioxide to obtain a reaction mixture containing propylene carbonate.

Although the present process may tolerate the presence of minor amounts of water, alcohols and diols, it is preferably performed in essential absence of water in order to avoid side reactions between water and the propylene oxide and/or the propylene carbonate formed.

Preferably, the combined process feeds, including the recycled catalyst, contain from 0% to 10% by weight of water. More preferably, the feeds contain from 0% to 5% by weight of water, again more preferably from 0% to 2% by weight.

The subject process employs a tetraalkyl phosphonium bromide catalyst of the formula $R^1R^2R^3R^4PBr$ (I). Tetraalkyl within the sense of the present invention means that the four alkyl substituents, $R^1$ to $R^4$, are covalently bonded to the phosphorus atom. Preferably, alkyl substituent means a saturated hydrocarbon radical having from 1 to 10 carbon atoms, more preferably from 1 to 6 carbon atoms, again more preferably from 2 to 4 carbon atoms, and most preferably 4 carbon atoms. Accordingly, the preferred alkyl substituents $R^1$ to $R^4$ are preferably selected from the group consisting of methyl, ethyl, n-propyl, isopropyl, n-butyl, isobutyl and tertiary butyl, the most preferred alkyl substituent being n-butyl.

In the process of the present invention, the tetraalkylphosphonium bromide catalyst has a surprisingly good activity and selectivity for the desired products while being extremely stable. Another important advantage of the catalyst is its low tendency to inflict corrosion.

Within the quaternary phosphonium halide family, the properties of the catalyst in the subject process have been found to depend on the halide counter-ion, as well as on the structure of the phosphonium moiety. Halides are ions of F, Cl, Br, I and At. Of these, astatine-containing compounds were not evaluated due to the radioactivity of the element and its low availability. Additionally, quaternary phosphonium fluorides were not evaluated due to the low environmental acceptance of fluorine-containing side products.

Phosphonium chlorides were found to decompose significantly faster than phosphonium iodides and bromides in the process of the present invention. This phenomenon is enhanced when the catalyst is continuously recycled from the product mixture to the reaction vessel. Such behavior renders the use of a chloride-containing catalyst undesirable for the present reaction.

Under the conditions of the present process, quaternary phosphonium bromides have been found to give a higher activity than the corresponding iodides. An additional disadvantage of iodide-containing catalysts is that their decomposition products have boiling points close to those of the desired products of the subject process, making them difficult to remove. Contrary to this, the boiling points of most bromide-containing decomposition products of tetraalkyl phosphonium bromide are not close to those of the desired end products. Also, the eventual release of iodine is undesirable from an environmental point of view, as by far less free iodine than bromine is present in seawater or living organic cells. Therefore, the treatment of waste streams containing iodides would necessitate use of cumbersome purification treatments. Hence, the use of iodide-containing phosphonium catalysts is equally undesirable for the present reaction.

Within the group of tetraalkyl phosphonium bromides, symmetrically substituted tetraalkyl phosphonium bromides, i.e. those wherein the four alkyl substituents are identical alkyl radicals, were found to be more stable than asymmetrically substituted phosphonium bromides at similar activity levels. Accordingly, a tetraalkyl phosphonium bromide catalyst of the formula $R^1R^2R^3R^4PBr$ (I), wherein $R^1$, $R^2$, $R^3$ and $R^4$ in formula (I) represent identical alkyl groups is preferably used in the subject process.

An additional advantage for the use of a symmetrically substituted tetraalkyl phosphonium bromide catalyst resides in the fact that simpler decomposition product mixtures are formed than by using asymmetrically substituted phosphonium catalysts. This allows a more efficient purification of the desired end products.

Particularly good results were obtained with tetrabutyl phosphonium bromide. Therefore, the present invention preferably relates to the subject process, wherein each of $R^1$, $R^2$, $R^3$ and $R^4$ in formula (I) represents an n-butyl radical, i.e. the subject process wherein tetra-n-butyl phosphonium bromide is used as the catalyst. This catalyst has the further advantage that it has a melting point in the temperature range usually employed for the subject process. Therefore, it usually is a liquid during the initial process phase. It also dissolves more readily in the formed products, and to some extent already in the propylene oxide in the absence of a solvent.

The conversion with the help of the phosphonium bromide catalyst may be conducted at varying catalyst concentrations. The determination of a particular effective concentration largely depends on the process parameters, such as, for instance, residence time of the process feeds in the reactor, type of feed, temperature and pressure.

The amount of catalyst may conveniently be expressed in mole catalyst per mole propylene oxide. Preferably due to a lower amount of by-products, the subject process is performed in the presence of at least 0.0001 mole of the tetraalkyl phosphonium bromide catalyst per mole propylene oxide.

Preferably, the amount of tetraalkyl-phosphonium bromide compound present is such that there is from 0.0001 to 0.1 mole of tetraalkyl-phosphonium bromide compound per mole propylene oxide, more preferably from 0.001 to 0.05, and most preferably from 0.003 to 0.03 of mol catalyst per mole propylene oxide.

Preferably, a protogenic compound is present during the conversion of propylene oxide with carbon dioxide into the propylene carbonate. A protogenic compound is a compound capable of acting as a proton donor, such as a hydrogen bond donor solvent (as defined in Pure Applied Chem., 66, 1077-1184, 1994). The presence of a protogenic compound helps in dissolving the catalyst and the feeds, and permits the introduction of fresh or recycled catalyst to the reaction in the form of a liquid stream that can be pumped back into the reactor. Preferably, the protogenic compound is an alcohol. A specific preferred compound is the 1,2-propanediol derived from the propylene oxide used. Such mono-glycol hydrolysis product of the 1,2-propanediol may be obtained directly from the propylene oxide or from the propylene oxide via the corresponding propylene carbonate. The use of the corresponding 1,2-propanediol avoids the introduction of additional products into the process and simplifies product purification.

The insertion of carbon dioxide into the oxirane moiety of propylene oxides is a reversible reaction, i.e. propylene oxide may also be formed back from propylene carbonate under release of carbon dioxide. In order to shift the equilibrium towards the desired propylene carbonates, the reaction is preferably performed under increased pressure.

Besides providing for the desired surplus of carbon dioxide, operation at increased pressure also allows the reaction to be conducted essentially in the liquid phase, as propylene oxide will largely remain liquid under the process conditions.

This may preferably be achieved by conducting the subject process at a total pressure in the range of from to 5 to $200 \times 10^5$ N/m$^2$ (i.e. 5 to 200 bar), the partial carbon dioxide pressure preferably being in the range of from to 5 to $70 \times 10^5$ N/m$^2$, more preferably in the range of from to 7 to $50 \times 10^5$ N/m$^2$, and most preferably in the range of from to 10 to $20 \times 10^5$ N/m$^2$.

A large number of different contaminants are allowed to be present in the manufacture of propylene carbonate according to the present invention. However, it was found that when the feeds contained traces of chloride, the stability of the present bromide catalysts was decreased. This effect is especially prominent when the catalyst has been recycled frequently under addition of fresh feed. Accordingly, the present process is preferably conducted by using a feed containing less than 1000 ppmw of chloride, more preferably less than 100 ppmw of chloride calculated on the total weight of the feed.

The catalyst of the present invention is a recycled tetraalkylphosphonium bromide catalyst. The expression recycled means that the tetraalkylphosphonium bromide was applied previously in the manufacture of propylene carbonate from propylene oxide and carbon dioxide. Generally, the catalyst will have been used in the process, separated from the propylene carbonate or from a product derived from the propylene carbonate, and again contacted with propylene oxide and carbon dioxide.

The present process may be integrated with a process for the manufacture of 1,2-propanediol. Accordingly, the present invention also pertains to a process for the preparation of 1,2-propanediol, which process comprises:

(i) preparing propylene carbonate in a process according to the present invention, (ii) contacting the reaction mixture containing the propylene carbonate with water and/or alcohol in the presence of a heterogeneous catalyst to obtain 1,2-propanediol and optionally dialkylcarbonate, and (iii) separating the 1,2-propanediol and optionally dialkylcarbonate from the reaction mixture obtained.

Preferably, the reaction mixture containing the propylene carbonate is contacted with water only. If the propylene carbonate is solely contacted with water, the product of the process is 1,2-propanediol only.

Although part of the reaction mixture obtained in step (i) may be removed from the process, it is generally preferred to subject all or substantially all of the reaction mixture obtained to step (ii).

Suitable heterogeneous catalysts for use in step (ii) are well known and are described for instance in JP-A-06/238165 or EP-A-0,478,073 hereby incorporated by reference. By integration of the process for the preparation of an propylene carbonate with the process for the preparation of a 1,2-propanediol, side reactions that lead to the formation of di- and tri-propylene glycols in one-pot processes may be largely suppressed. Such side-reactions have been described in GB A-2,035,294. The process of the present invention results in an overall higher yield of the desired products. The present process was found to give exceptionally good results for the manufacture of 1,2-propanediol. This is thought to be related to the solvent properties and pH of the propylene oxide feed, which differ largely from for instance ethylene oxide feeds.

The integrated process comprises conversion of propylene carbonate with water or alcohol, preferably methanol, to obtain 1,2-propanediol and optionally dialkylcarbonate. In order to recycle the present phosphonium bromide catalyst, the catalyst is separated from the reaction mixture, preferably when the reaction mixture is separated anyway. It is especially advantageous to remove the tetraalkyl-phosphonium bromide catalyst together with 1,2-propanediol. The 1,2-propanediol solubilizes the catalyst which permits simpler handling. A further advantage of such separation is that the 1,2-propanediol can remain with the catalyst as the 1,2-propanediol is beneficial upon recycle to process step (i). Therefore, it is preferred that in step (iii) of the present invention the tetraalkyl-phosphonium bromide catalyst is removed in combination with 1,2-propanediol, which catalyst and 1,2-propanediol are subsequently recycled to step (i).

The process according to the present invention is further illustrated by the following examples.

EXAMPLE 1

Carbon dioxide and propylene oxide were contacted in a first reactor at a temperature of 180° C. and a pressure of 20 bar at a carbon dioxide partial pressure of $20 \times 10^5$ N/m² with a tetrabutyl-phosphonium bromide catalyst in a molar ratio of catalyst to propylene oxide of 1:60. The amount of propylene oxided added was 10 kg of propylene oxide per kg of tetrabutylphosphonium bromide catalyst per hour.

NMR, and is expressed as % of phosphorus atoms of the phosphonium compound that had decomposed to the phosphine oxide.

The results of the examples are summarized in Table 1. It is clear that the tetrabutyl chloride catalyst is unstable at the demanding operating conditions. The tetraalkyl phosphonium bromides outperform the other catalysts used in terms of yields versus catalyst stability. Tetra-n-butyl phosphonium bromide shows the best overall performance.

TABLE 1

| Experiments | Catalyst | Reaction time [h] | Catalyst intake [mg] | Propylene Carbonate yield [mole %] | 1,2-Propanediol yield [mole %] | Catalyst degradation [% of phosphorus atoms] |
|---|---|---|---|---|---|---|
| Experiment 1 | Bu₄PBr | 4 | 136 | 64.8 | 0.3 | not determined |
| Experiment 2 | Bu₄PBr | 4 | 505 | 92.9 | 0.7 | 6.8 |
| Experiment 3 | Et₄PBr | 4 | 516 | 92.7 | 0.5 | 10.5 |
| Comparative Experiment 2 | Bu₄PCl | 4 | 509 | 93.4 | 0.3 | 29.8 |
| Comparative Experiment 3 | Bu₄PI | 4 | 488 | 72.0 | 0.4 | 11.9 |
| Comparative Experiment 5 | MeBu₃PI | 4 | 492 | 75.1 | 0.3 | 15.2 |
| Comparative Experiment 6 | MePh₃PBr | 4 | 514 | 70.3 | 0.2 | 69.9 |

Subsequently, gaseous carbon dioxide was removed in a gas-liquid separator operating at a pressure of 20 bar and a temperature of 80° C.

The liquid reaction mixture obtained was sent to a second reactor. The second reactor contained heterogeneous alumina catalyst and was operated at 150° C. and $25 \times 10^5$ N/m². The molar ratio of water to propylene carbonate was about 1.2:1.

1,2-propanediol was separated from the reaction mixture by distillaton. One of the fractions obtained contained 1,2-propanediol in combination with 33% wt of tetrabutylphosphonium bromide catalyst. This fraction was recycled to the first reactor.

The process was operated at high conversion and selectivity for over 600 hours without addition of fresh catalyst. This shows that the catalyst is extremely stable at these demanding operating conditions.

EXAMPLE 2

The experiments were carried out in a 60 ml Hastelloy C (Hastelloy is a trademark of Haynes International, Inc.) autoclave reactor equipped with a heating jacket and a gas inlet, and stirred by means of a gas-dispersing propeller.

Following placement of the evaluated catalyst into the reactor, 5 g (86 mmoles) of propylene oxide (PO) were added.

The reactor was then sealed and carbon dioxide ($CO_2$) was introduced to a total pressure of $20 \times 10^5$ N/m² (bar). Then the reactor was heated to 180° C. under stirring. At 180° C., the total reactor pressure was adjusted with $CO_2$ to $50 \times 10^5$ N/m² (bar). After 4 hours at the above-described conditions, the reactor was cooled down rapidly, allowed to decompress, and samples were taken.

The yields in propylene carbonate (PC) and 1,2-propanediol (monopropyleneglycol, MPG) were determined by gas chromatography (GC) using decane as an external standard, and expressed as mole %, based on the amount of moles of converted propylene oxide. Catalyst decomposition to the corresponding phosphine oxide was determined using 31P-

What is claimed:

1. A process for the preparation of a propylene carbonate, which process comprises contacting propylene oxide with carbon dioxide at a temperature of from 150° C. to 250° C. in the presence of a recycled tetraalkyl-phosphonium bromide catalyst of the formula $R^1R^2R^3R^4PBr$ wherein each of $R^1$, $R^2$, $R^3$, and $R^4$ are alkyl substituents.

2. A process of claim 1, wherein a protogenic compound is present during the preparation of propylene carbonate.

3. The process of claim 1, wherein the protogenic compound is an alcohol.

4. The process of claim 1, wherein $R^1$, $R^2$, $R^3$ and $R^4$ represent identical alkyl groups.

5. The process of claim 1, wherein the amount of tetraalkyl phosphonium bromide compound is from 0.0001 to 0.1 mole per mole of propylene oxide.

6. The process of claim 1, wherein the preparation of propylene carbonate is conducted at a partial carbon dioxide pressure in the range of from 5 to $70 \times 10^5$ N/m².

7. A process for the preparation of 1,2-propanediol, which process comprises:
   (i) preparing a propylene carbonate as claimed in claim 1 to obtain a reaction mixture;
   (ii) contacting the reaction mixture containing the propylene carbonate with water and/or alcohol in the presence of a heterogeneous catalyst to obtain 1,2-propanediol and optionally dialkylcarbonate; and,
   (iii) separating the 1,2-propanediol and optionally dialkylcarbonate from the reaction mixture obtained.

8. The process of claim 7, wherein in step (ii) the propylene carbonate is contacted with water to obtain 1,2-propanediol.

9. The process of claim 7, wherein in step (iii) the tetraalkylphosphonium bromide catalyst is removed in combination with 1,2-propanediol, which catalyst and 1,2-propanediol are subsequently recycled to step (i).

10. The process of claim 7, wherein a protogenic compound is present during the preparation of propylene carbonate.

11. The process of claim 10, in which process the protogenic compound is an alcohol.

12. The process of claim 5, wherein $R^1$, $R^2$, $R^3$ and $R^4$ represent identical alkyl groups.

13. The process of claim 7, wherein the amount of tetraalkyl phosphonium bromide compound is from 0.0001 to 0.1 mole per mole of propylene oxide.

14. The process of claim 7, wherein the preparation of propylene carbonate is conducted at a partial carbon dioxide pressure in the range of from 5 to $70 \times 10^5$ N/m$^2$.

* * * * *